United States Patent

Buysch et al.

[11] Patent Number: 5,663,408
[45] Date of Patent: Sep. 2, 1997

[54] PROCESS FOR PREPARING DIARYL CARBONATES

[75] Inventors: Hans-Josef Buysch; Carsten Hesse, both of Krefeld; Johann Rechner, Kempen, all of Germany

[73] Assignee: Bayer Aktiengesellschaft, Leverkusen, Germany

[21] Appl. No.: 623,728

[22] Filed: Mar. 29, 1996

[30] Foreign Application Priority Data

Apr. 5, 1995 [DE] Germany ............... 195 12 616.5

[51] Int. Cl.$^6$ ............... C07C 68/00; C07C 69/96
[52] U.S. Cl. ............... 558/274
[58] Field of Search ............... 558/274

[56] References Cited

FOREIGN PATENT DOCUMENTS

| | | |
|---|---|---|
| 0350697 | 1/1990 | European Pat. Off. . |
| 0350700 | 1/1990 | European Pat. Off. . |
| 0450442 | 10/1991 | European Pat. Off. . |
| 0503581 | 9/1992 | European Pat. Off. . |
| 0507546 | 10/1992 | European Pat. Off. . |
| 0583935 | 2/1994 | European Pat. Off. . |
| 0583937 | 2/1994 | European Pat. Off. . |
| 0583938 | 2/1994 | European Pat. Off. . |
| 2815501 | 10/1979 | Germany . |
| 2815512 | 10/1989 | Germany . |
| 1578713 | 11/1980 | United Kingdom . |
| 9303000 | 2/1993 | WIPO . |

*Primary Examiner*—Johann Richter
*Assistant Examiner*—Michael G. Ambrose
*Attorney, Agent, or Firm*—Sprung Horn Kramer & Wood

[57] ABSTRACT

In the preparation of diaryl carbonates from an aromatic hydroxy compound, CO and $O_2$, use is made not only of a quaternary salt, a base, a platinum metal catalyst and a cocatalyst, but additionally of a heterogeneous promoter which is a compound of the formula $$A_xB_yC_z,$$

where

A and B are each, independently of one another, an element of group IIIA, IVA, VA, IIIB, IVB, VB, VIB or VIIB of the Periodic Table of the Elements (Mendeleev), C represents an element of the 2nd period of the Periodic Table of the Elements (Mendeleev), x is a number from 1 to 3, y is a number from 0 to 3 and z is a number from 1 to 12.

20 Claims, No Drawings

PROCESS FOR PREPARING DIARYL CARBONATES

BACKGROUND OF THE INVENTION

The present invention relates to a process for preparing diaryl carbonates by reaction of an aromatic hydroxy compound (e.g. phenol) with carbon monoxide and oxygen at elevated temperature in the presence of a base, a quaternary salt, a catalyst and a cocatalyst, which is characterized in that it is carried out in the presence of a heterogeneous promoter.

It is known that organic carbonates can be prepared by oxidative reaction of aromatic hydroxy compounds with carbon monoxide in the presence of a platinum metal catalyst (German Offenlegungsschrift 28 15 512). The platinum metal preferably used is palladium. In addition, a cocatalyst (e.g. manganese or cobalt salts), a base, a quaternary salt, various quinones or hydroquinones and desiccants can be used. The reaction can be carried out in a solvent, preferably methylene chloride.

Only small space-time yields can be achieved using these processes, so that long residence times are required. A rapid fall in the activity of the catalyst occurs during the reaction, and finally the catalyst activity is completely exhausted.

The use of various copper salts as cocatalyst proposed in EP-503 581 does not lead to higher space-time yields. Here too, the activity of the catalyst falls steadily and quickly until the catalyst is completely inactive.

The use of considerable amounts of various quinones or hydroquinones as electron transfer catalyst, as proposed in various applications (EP 350 697, EP 350 700, EP 450 442, EP 503 581, EP 550 743, etc.), improves neither the space-time yield nor does it solve the problem of deactivation of the catalyst. On the contrary, the selectivity and thus the economics of the process are considerably reduced by the formation of by-products.

The applications EP 583 935, EP 583 937, EP 583 938 relate to a cobalt catalyst containing a pentadentate ligand, specifically the cobalt di(salicylyl)-3,3'-diamino-N-methyldipropylamine (CoSMDP), which is used in combination with terpyridine. The synthesis of this complex has many stages and is complicated. Under the reaction conditions specified, these compounds are not stable so that the losses caused by decomposition have to be replaced at high cost, which makes it impossible to carry out the process economically. Even the use of such highly active and difficult-to-prepare cocatalysts cannot prevent the activity of the catalyst being reduced to half after only 2 hours.

It was therefore an object of the invention to find a catalyst system having high activity and high operating life which allows the preparation of aromatic carbonates under economical and industrially realizable conditions.

SUMMARY OF THE INVENTION

It has now surprisingly been found that the operating life of the catalyst in the preparation of diaryl carbonates by oxidative reaction of an aromatic hydroxy compound in the presence of a platinum metal catalyst, a cocatalyst, a quaternary salt and a base can be increased by carrying out the reaction in the presence of a heterogeneous promoter. The reason for the deactivation of the platinum metal catalyst is not known. All the more surprising is the fact that the operating life of the platinum metal catalyst can be increased by addition of an inert component as which a heterogeneous promoter has to be regarded.

The invention accordingly provides a process for preparing diaryl carbonates of the formula $$RO-CO-OR$$

by reaction of an aromatic hydroxy compound of the formula $$ROH,$$

where, in the formulae,

R is substituted or unsubstituted $C_6$–$C_{12}$-aryl, preferably substituted or unsubstituted phenyl, particularly preferably unsubstituted phenyl, with CO and $O_2$ at a temperature of from 30° to 200° C., preferably from 30° to 150° C., particularly preferably from 40° to 120° C., and a pressure of from 1 to 150 bar, preferably from 2 to 50 bar, particularly preferably from 5 to 25 bar, in the presence of a quaternary salt, a base, a platinum metal catalyst and a cocatalyst, characterized in that it is carried out in the additional presence of a heterogeneous promoter which is a compound of the formula $$A_xB_yC_z$$

where

A and B are each, independently of one another, an element of group IIIA, IVA, VA, IIIB, IVB, VB, VIB or VIIB of the Periodic Table of the Elements (Mendeleev), C represents an element of the 2nd period of the Periodic Table of the Elements (Mendeleev), x is a number from 1 to 3, y is a number from 0 to 3 and z is a number from 1 to 12.

DETAILED DESCRIPTION OF THE INVENTION

For the example of the formation of diphenyl carbonate, the process of the invention can be represented in terms of formulae as follows:

$$2C_6H_5-OH+CO+\tfrac{1}{2}O_2 \rightarrow (C_6H_5O)_2CO+H_2O.$$

The heterogeneous promoters to be used in the process of the invention are preferably compounds in which C represents boron, carbon, nitrogen or oxygen.

Preference is given to using metal oxides, carbides, nitrides or borides or a carbon-containing material.

Examples of such compounds which may be mentioned, without the process of the invention being limited to these, are α-aluminium oxide, γ-aluminium oxide, aluminium carbide, aluminium nitride, silicon dioxide, silicon carbide, silicon nitride, titanium dioxide, titanium boride, titanium carbide, titanium nitride, zirconium dioxide, zirconium boride, zirconium nitride, cerium dioxide, dysprosium oxide, vanadium pentoxide, vanadium boride, vanadium carbide, vanadium nitride, molybdenum carbide, tungsten boride, tungsten nitride, tungsten carbide, manganese dioxide, bismuth oxide, lead molybdate and lead titanate.

Further preferred promoters to be used in the process of the invention are carbon-containing materials where A as an element of group IVA and C are both carbon and y is zero. Examples of carbon-containing materials are carbon black, graphite, carbon fibres and porous carbons such as coke, wood charcoal and activated carbon. Preference is given to using carbon black or activated carbon. For use in the process of the invention, the activated carbons and carbon blacks can be from vegetable (e.g. wood, peat, nut shells, coffee beans), animal (e.g. blood, bones) or mineral raw materials (e.g. brown coal, black coal, petrochemical hydrocarbons).

Suitable aluminium oxides can be in crystalline form in various modifications, for example as α-aluminium oxides, γ-aluminium oxides, η-aluminium oxides, κ-aluminium oxides or ρ-aluminium oxides. However, they can also contain amounts of amorphous material. It is possible to use naturally occurring or synthetic aluminium oxides. The aluminium oxides, preferably naturally occurring, can contain small amounts of other elements such as alkali and alkaline earth metals, iron or silicon. Preference is given to using products containing <2% by weight, particularly preferably <1% by weight, of such impurities. Synthetic aluminium oxides are particularly pure. It is possible to use acid, neutral and basic oxides. Such aluminium oxides and their origin or preparation processes for such compounds are described, for example, in Kirk-Othmer, Encyclopedia of Chemical Technology, 3rd Edition, Vol. 2, p. 218 ff., New York 1978, or Ullmann's Encyclopedia of Industrial Chemistry, 5th Edition, Vol. A1, p. 557 ff., Weinheim 1985. Suitable aluminium oxides are both those from natural sources, i.e. from various aluminium minerals, and those from other aluminium-containing precursors such as aluminium salts, aluminium alkoxides and organoaluminium compounds. For the purposes of the invention, preferred aluminium oxides are so-called "activated aluminium oxides". These can be amorphous, partially crystalline or crystalline (e.g. $\gamma$-$Al_2O_3$ or $\eta$-$Al_2O_3$). Further preferred aluminium oxides are α-aluminium oxides having BET surface areas $\geq 2$ $m^2/g$.

Suitable titanium oxides can be used in the orthorhombic (brookite) or tetragonal modification (anatase, rutile), but can also contain amounts of amorphous material. Such titanium oxides and their origin or preparation processes for such compounds are described, for example, in Kirk-Othmer, Encyclopedia of Chemical Technology, 3rd Edition, Vol. 17, p. 801 ff., New York 1978, or Vol. 23, p. 139 ff. Suitable titanium oxides for use in the process of the invention are both titanium oxides from natural sources, i.e. from various titanium minerals, and synthetic oxides from other titanium-containing precursors such as titanium salts, titanium halides, titanium alkoxides and organotitanium compounds. Likewise suitable for use in the process of the invention are titanium oxides whose surfaces have subsequently been modified and which are commercially available in this form. The titanium oxides can contain small amounts of other elements such as alkali and alkaline earth metals, iron or silicon. Preference is given to products containing <2% by weight, particularly preferably <1% by weight, of such impurities. Synthetic titanium oxides are particularly pure.

Zirconium oxides can occur in various modifications, some of which can be reversibly converted into one another at certain temperatures and pressures. Zirconium oxides and their origin or preparation processes for such compounds are described, for example, in Kirk-Othmer, Encyclopedia of Chemical Technology, 2nd Edition, Vol. 11, p. 729 ff., New York 1978, and Vol. 24, p. 882 ff., or Ullmann's Encyclopedia of Industrial Chemistry, 4th Edition, Vol. 24, p. 695 ff., Weinheim 1983. Suitable zirconium oxides for use in the process of the invention are both those from natural sources, i.e. from various zirconium minerals, and also those from other zirconium-containing precursors such as zirconium salts, zirconium alkoxides and organozirconium compounds. For the purposes of the invention, preferred zirconium oxides are so-called "stabilized zirconium oxides" which can contain small amounts of calcium oxide, magnesium oxide or yttrium oxide.

Suitable oxides of the lanthanides can occur in various modifications, some of which can be reversibly converted into one another at certain temperatures and pressures. Among the oxides of the lanthanides, cerium dioxide ($CeO_2$) and dysprosium oxide are preferred. Cerium dioxide can display deviations from the stoichiometry, so that in the formula $CeO_{2-x}$, x can assume a value of from 0 to 0.3. Cerium oxides and their origin or preparation processes for such compounds are described, for example, in Kirk-Othmer, Encyclopedia of Chemical Technology, 3rd Edition, Vol. 11, p. 729 ff., New York 1978, and Vol. 24, p. 882 ff. or Ullmann's Encyclopedia of Industrial Chemistry, 4th Edition, Vol. 24, p. 695 ff., Weinheim 1983. Suitable cerium oxides for use in the process of the invention are both those from natural sources, i.e. from various cerium minerals, and also those from other cerium-containing precursors such as cerium oxalates or hydroxides. It is possible to use naturally occurring or synthetic cerium oxides. For the purposes of the invention, preferred cerium oxides can also contain small amounts of other lanthanides (e.g. in the form of $Pr_6O_{11}$).

Suitable vanadium oxides can occur in various modifications, but can also contain amounts of amorphous material. Preference is given to vanadium pentoxide. Vanadium oxides and their origin or preparation processes for such compounds are described, for example, in Kirk-Othmer, Encyclopedia of Chemical Technology, 3rd Edition, Vol. 11, p. 729 ff., New York 1978, and Vol. 24, p. 882 ff. or Ullmann's Encyclopedia of Industrial Chemistry, 4th Edition, Vol. 24, p. 695 ff., Weinheim 1983. Suitable vanadium oxides for use in the process of the invention are both those from natural sources, i.e. from various vanadium minerals, and also those from other vanadium-containing precursors such as vanadium salts, vanadium alkoxides and organovanadium compounds. It is possible to use naturally occurring or synthetic vanadium oxides.

Nitrides suitable for the process of the invention are compounds of nitrogen and a metal or semimetal. Preference is given to the so-called "metal-like" nitrides such as vanadium nitride, titanium nitride or tungsten nitride, and the so-called "covalent" nitrides such as boron nitride, silicon nitride or aluminium nitride. Nitrides and preparation processes for such compounds are described, for example, in Kirk-Othmer, Encyclopedia of Chemical Technology, 3rd Edition, Vol. 15, p. 871 ff., New York 1978, or Ullmann's Encyclopedia of Industrial Chemistry, 4th Edition, Vol. 17, p. 315 ff., Weinheim 1979.

Carbides suitable for the process of the invention are binary compounds of elements with carbon, which can be prepared quite generally by action of elemental carbon or hydrocarbons on metals and metal compounds at appropriately high temperatures. Preference is given to the so-called "metal-like" carbides such as chromium carbide, hafnium carbide, molybdenum carbide, niobium carbide, tantalum carbide, vanadium carbide, titanium carbide or tungsten carbide, and the so-called "covalent" carbides such as boron carbide or silicon carbide. Carbides and preparation processes for such compounds are described, for example, in Kirk-Othmer, Encyclopedia of Chemical Technology, 3rd Edition, Vol. 4, p. 476 ff., New York 1978, or Ullmann's Encyclopedia of Industrial Chemistry, 5th Edition, Vol. A5, p. 61 ff., Weinheim 1986.

Borides suitable for the process of the invention are compounds of metals with boron, for example aluminium boride, vanadium boride, titanium boride, zirconium boride, iron boride, cobalt boride or tungsten boride. Borides and preparation processes for such compounds are described, for example, in Kirk-Othmer, Encyclopedia of Chemical Technology, 3rd Edition, Vol. 4, p. 123 ff., New York 1978, or Ullmann's Encyclopedia of Industrial Chemistry, 5th Edition, Vol. A4, p. 303 ff., Weinheim 1985.

Preferred promoters have BET surface areas of from 0.5 to 1500 m²/g, particularly preferably from 1 to 1500 m²/g and very particularly preferably from 2 to 1400 m²/g.

The promoters can be used as powder or as shaped bodies and can be separated off after the reaction, for example by filtration, sedimentation or centrifugation. If arranged as a fixed bed, the promoters are preferably used as shaped bodies, for example as spheres, cylinders, rods, hollow cylinders, rings, etc. When working in suspension in stirred vessels or bubble columns, the heterogeneous promoters are used in amounts of from 0.001 to 50% by weight, preferably from 0.01 to 10% by weight, particularly preferably from 0.1 to 5% by weight, based on the amount of aromatic hydroxy compound. In the case of a continuous procedure in counter-current or cocurrent or in the downflow mode over a fixed-bed promoter, weight hourly space velocities of from 0.1 to 20 g of aromatic hydroxy compound per g of promoter and hour, preferably from 0.2 to 10 g, particularly preferably from 0.2 to 5 g, are set.

The promoters used in a batchwise procedure can be repeatedly used without purification for the identical starting materials. If the starting materials are changed, the promoters are advantageously purified by extraction with inert solvents such as, for example, those mentioned further below as reaction media or with alcohols such as methanol, ethanol, isopropanol or butanol, with esters or amides of acetic acid or by treatment with superheated steam or air.

In a continuous method of operation, the heterogeneous promoters used can remain in the reactor for a long time. Regeneration can be carried out, if appropriate, by passing superheated steam over the promoter, optionally with addition of subordinate amounts of air (from about 0.1 to 20% by weight, based on the amount of steam used) at from 150° to 800° C. or by passing diluent gases, e.g. nitrogen or carbon dioxide, containing from 0.01 to 20% by weight of oxygen over the promoter, or by means of carbon dioxide alone, at from 200° to 800° C. The preferred regeneration temperature is from 250° to 700° C., particularly preferably from 250° to 600° C.

The aromatic hydroxy compounds to be used in the process of the invention are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A, preferably phenol. If the aromatic hydroxy compound is substituted, there are generally 1 or 2 substituents which are $C_1$–$C_4$-alkyl, $C_1$–$C_4$-alkoxy, fluorine, chlorine or bromine.

For the process of the invention, any organic or inorganic bases or mixtures thereof can be used. Examples of inorganic bases which may be mentioned are, without restricting the process of the invention, alkali metal hydroxides and carbonates, carboxylates or other salts of weak acids and also alkali metal salts of aromatic hydroxy compounds of the formula (II), e.g. alkali metal phenoxides. Of course, it is also possible to use the hydrates of alkali metal phenoxides in the process of the invention. An example of such a hydrate which may be mentioned here, without restricting the process of the invention, is sodium phenoxide trihydrate. However, the amount of water added is preferably such that a maximum of 5 mol of water are used per mol of base. Higher water concentrations lead, inter alia, to poorer conversions and decomposition of the carbonates formed. Organic bases which may be mentioned, without restricting the process of the invention, are tertiary amines which can bear $C_6$–$C_{10}$-aryl, $C_7$–$C_{12}$-aralkyl and/or $C_1$–$C_{20}$-alkyl radicals or are pyridine bases or are hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound which is also to be reacted to form the organic carbonate. These alkali metal salts can be lithium, sodium, potassium, rubidium or caesium salts. Preference is given to using lithium, sodium and potassium phenoxide, particularly preferably sodium phenoxide.

The base can be added to the reaction mixture as a pure compound in solid form or as a melt. In a further embodiment of the invention, the base is added to the reaction mixture as a solution containing from 0.1 to 80% by weight, preferably from 0.5 to 65% by weight, particularly preferably from 1 to 50% by weight, of the base. Solvents which can be used here are alcohols or phenols, such as the phenol to be reacted, or inert solvents. Examples which may be mentioned are those mentioned further below as reaction media. These solvents can be used alone or in any combination with one another. Thus, an embodiment of the process of the invention comprises, for example, dissolving the base in a phenol melt which has been diluted with a solvent. The base is preferably dissolved in the melt of an aromatic hydroxy compound, particularly preferably in a melt of the aromatic hydroxy compound which is to be reacted to form the organic carbonate. Very particularly preferably, the base is added in solution in phenol. The base is added in an amount which is independent of the stoichiometry. The ratio of platinum metal to base is preferably selected such that from 0.1 to 500, preferably from 0.5 to 200, particularly preferably from 0.9 to 130, equivalents of base are used per mol of platinum metal.

The process of the invention is preferably carried out without solvent. Of course, inert solvents can also be used. Examples of solvents which may be mentioned are dimethylacetamide, N-methylpyrrolidinone, dioxane, t-butanol, cumyl alcohol, isoamyl alcohol, tetramethylurea, diethylene glycol, halogenated hydrocarbons (e.g. chlorobenzene or dichlorobenzene) and ethers.

The platinum metal catalysts suitable for the process of the invention comprise at least one noble metal of group VIIIB, preferably palladium. In the process of the invention, the platinum metal can be added in various forms. Palladium can be used, for example, in metallic form or preferably in the form of palladium compounds of the oxidation states 0 or +2, for example palladium(II) acetylacetonate, halides or a complex containing platinum metal halide, which compound can additionally contain, for example, olefins, amines, phosphines, nitriles, carbon monoxide or water, for example $A_2(PdHal_4)$, where A represents, for example, Li, Na, K, $NH_4$, Rb, Cs, $NR_4$ and R represents an organic radical $C_6$–$C_{10}$-aryl, $C_7$–$C_{12}$-aralkyl and/or $C_1$–$C_{20}$-alkyl and Hal represents a halogen such as, for example, F, Cl, Br, I, palladium(II) carboxylates of $C_2$–$C_6$-carboxylic acids, nitrate, oxides or other palladium complexes which can contain, for example, olefins, amines, phosphines, nitriles, carbon monoxide, water and/or halides. Particular preference is given to palladium bromide and palladium acetylacetonate. The amount of platinum metal catalyst is not restricted in the process of the invention. Preference is given to using an amount of catalyst such that its concentration, calculated as metal, in the reaction mixture is from 1 to 3000 ppm, particular preference being given to concentrations of from 10 to 1000 ppm, very particularly preferably from 20 to 1000 ppm.

The cocatalyst used for the process of the invention is a metal compound of group IB, IIB, IIIB, IVB, VB, VIB or VIIB of the Periodic Table of the Elements (Mendeleev), where the metal can be used in various oxidation states. Without restricting the process of the invention, mention may be made of manganese(II), manganese(III), copper(I), copper(II), cobalt(II), cobalt(III), vanadium(III) and vanadium(IV). The metals can be used, for example, as halides, oxides, carboxylates of $C_2$–$C_6$-carboxylic acids, diketonates or nitrates and also as complexes which can contain, for example, carbon monoxide, olefins, amines, phosphines and/or halides. Preference is given to using manganese compounds in the process of the invention, particularly preferably manganese(II) complexes, very particularly preferably manganese(II) acetylacetonate. The cocatalyst is used in an amount such that its concentration is in the range from 0.001 to 20% by weight of the reaction mixture, preference being given to the concentration range from 0.005 to 5% by weight, particularly preferably from 0.01 to 2% by weight.

The quaternary salts used for the purposes of the present invention can be, for example, ammonium or phosphonium salts substituted by organic radicals. Suitable salts for use in the process of the invention are ammonium and phosphonium salts which bear $C_6$–$C_{10}$-aryl, $C_7$–$C_{12}$-aralkyl and/or $C_1$–$C_{20}$-alkyl radicals as organic radicals and a halide, tetrafluoroborate or hexafluorophosphate as anion. In the process of the invention, preference is given to ammonium salts which bear the specified organic radicals and a halide as anion, particular preference being given to tetrabutylammonium bromide. The amount of such a quaternary salt is from 0.1 to 50% by weight, based on the weight of the reaction mixture. This amount is preferably from 0.5 to 15% by weight, particularly preferably from 1 to 10% by weight.

The process of the invention is, preferably without solvent, carried out at from 30° to 200° C., preferably at from 30° to 150° C., particularly preferably at from 40° to 120° C., and at a pressure of from 1 to 150 bar, preferably from 2 to 50 bar, particularly preferably at from 5 to 25 bar.

The process of the invention can be carried out in different variants. One possibility is a batchwise procedure. Here, CO and oxygen are passed into the reaction mixture either by means of a gas-introduction stirrer (in the case of a stirred vessel) or other known gas distribution devices. The excess reaction gas continuously removes the water of reaction from the reactor. After the intended conversion is reached, the reaction mixture is removed from the reactor or, if desired, worked up in the reactor. In the preferred embodiments of the process of the invention, a continuous method of operation in a single reactor or in a cascade of reactors is used. For this purpose, the reactor used is a stirred vessel or a bubble column or a cascade of such reactors, with the cascade comprising from 2 to 15, preferably from 2 to 10, particularly preferably from 2 to 5, individual reactors.

The following examples clarify the process of the invention, but without restricting it to them.

EXAMPLES 1–13

In a ground-flange pot fitted with gas-introduction stirrer, condenser and downstream cold trap, 0.078 g of palladium bromide and 5 g of tetrabutylammonium bromide were dissolved at 55° C. in 300 g of phenol. To activate the catalyst, carbon monoxide (20 l/h) was passed through this solution for one hour. 0.76 g of manganese(II) acetylacetonate, 0.9 g of sodium phenoxide and 3 g of heterogeneous promoter (see table) were then added and the mixture was stirred while passing in a gas mixture of carbon monoxide and oxygen (95:5% by volume). The amount of gas mixture was set to 60 standard l/h. Every hour, a sample was taken from the reaction mixture and analysed by gas chromatography. The analyses indicated the diphenyl carbonate contents shown in the table.

| Ex. | Promoter | DPC-content [%] | | |
|---|---|---|---|---|
| | | 2 h | 15 h | 30 h |
| 1 | $V_2O_5$ | 1.23 | 9.37 | 18.77 |
| 2 | $MoC_2$ | 0.97 | 7.94 | 14.11 |
| 3 | $ZrO_2$ | 0.96 | 7.34 | 14.34 |
| 4 | $Al_2O_3$ (Rhone-Poulenc, SPH 512) | 0.69 | 6.09 | 12.63 |
| 5 | $CeO_2$ | 0.61 | 5.74 | 8.75 |
| 6 | Activated carbon (Strem, No. 06-100) | 1.02 | 7.31 | 15.86 |
| 7 | $TiO_2$ (Bayertitan PK 5585) | 1.00 | 7.71 | 14.92 |
| 8 | $Bi_2O_3$ | 1.21 | 9.44 | 17.91 |
| 9 | Activated carbon (Chemviron, Type CPG) | 0.90 | 6.77 | 13.07 |
| 10 | $ZrB_2$ | 0.87 | 6.98 | 13.06 |
| 11 | AlN | 0.77 | 5.55 | 11.99 |
| 12 | $Si_3N_4$ | 1.03 | 7.63 | 15.35 |
| 13 | $PbTiO_3$ | 0.66 | 5.28 | 9.67 |

Comparative Example 1

The experiment was repeated as described in Example 1, but it was carried out without a heterogeneous promoter. Gas-chromatographic analysis of the samples indicated that the reaction mixture contained 0.55% of diphenyl carbonate after 2 hours, 5.5% of diphenyl carbonate after 15 hours and 7.4% of diphenyl carbonate after 30 hours.

Comparative Example 2

The experiment was repeated as described in Example 1, but no palladium bromide was added. Gas-chromatographic analysis of the samples indicated that no diphenyl carbonate was present in the reaction mixture after ten hours. This example demonstrates that the promoter alone has no catalytic activity.

EXAMPLE 14

In an autoclave (1 l) fitted with gas-introduction stirrer, condenser and downstream cold trap, 0.34 g of palladium bromide and 8.31 g of tetrabutylammonium bromide were dissolved at 80° C. in 450 g of phenol. To activate the catalyst, carbon monoxide (3 l/h) was passed through this solution for one hour. 0.77 g of manganese(II) acetylacetonate and 2.21 g of sodium phenoxide, dissolved in 50 g of phenol, and 10 g of $V_2O_5$ were then added and the pressure was set to 10 bar while passing in a gas mixture of carbon monoxide and oxygen (95:5% by volume). The amount of gas mixture was set to 300 standard l/h. Every hour, a sample was taken from the reaction mixture and analysed by gas chromatography. The analyses indicated that the reaction mixture contained 13.0% of diphenyl carbonate after one hour, 18.0% of diphenyl carbonate after 2 hours and 21.5% of diphenyl carbonate after 3 hours. 19.6 g of a phenol/water mixture had condensed in the cold trap.

EXAMPLE 15

In an autoclave (1 l) fitted with gas-introduction stirrer, condenser and downstream cold trap, 0.080 g of palladium bromide and 8.31 g of tetrabutylammonium bromide were dissolved at 90° C. in 450 g of phenol. To activate the catalyst, carbon monoxide (3 l/h) was passed through this solution for one hour. 0.77 g of manganese(II) acetylacetonate and 2.21 g of sodium phenoxide, dissolved in 50 g of phenol, and 10 g of TiO₂ (Bayertitan PK 5585) were then added and the pressure was set to 11 bar while passing in a gas mixture of carbon monoxide and oxygen (95:5% by volume). The amount of gas mixture was set to 300 standard l/h. Every hour, a sample was taken from the reaction mixture and analysed by gas chromatography. The analyses indicated that the reaction mixture contained 12.1% of diphenyl carbonate after one hour, 17.5% of diphenyl carbonate after 2 hours and 20.3% of diphenyl carbonate after 3 hours. 16.6 g of a phenol/water mixture had condensed in the cold trap.

EXAMPLE 16

In an bubble column (volume=1 l) fitted with a ring of gas-introduction nozzles, condenser fitted on top and downstream cold trap, 0.080 g of palladium bromide and 8.31 g of tetrabutylammonium bromide were dissolved at 75° C. in 450 g of phenol. To activate the catalyst, carbon monoxide (10 l/h) was passed through this solution for one hour. 0.77 g of manganese(II) acetylacetonate and 2.21 g of sodium phenoxide, dissolved in 50 g of phenol, and 1 g of activated carbon (Strem, No. 06-100) were then added and the pressure was set to 8 bar while passing in a gas mixture of carbon monoxide and oxygen (96.5:3.5% by volume). The amount of gas mixture was set to 300 standard l/h. Every hour, a sample was taken from the reaction mixture and analysed by gas chromatography. The analyses indicated that the reaction mixture contained 9.3% of diphenyl carbonate after one hour, 15.2% of diphenyl carbonate after 2 hours and 18.3% of diphenyl carbonate after 3 hours. 15.6 g of a phenol/water mixture had condensed in the cold trap.

What is claimed is:

1. A process for preparing a diaryl carbonate of the formula

RO—CO—OR which comprises reacting an aromatic hydroxy compound of the formula

ROH, where, in the formulae,

R is substituted or unsubstituted $C_6$–$C_{12}$-aryl, with CO and $O_2$ at a temperature of from 30° to 200° C. and a pressure of from 1 to 150 bar in the presence of a quaternary salt, a base, a platinum metal catalyst and a cocatalyst, and in the additional presence of a heterogeneous promoter which is a compound of the formula $A_xB_yC_z$ where A and B are each, independently of one another, an element of group IIIA, IVA, VA, IIIB, IVB, VB, VIB or VIIB of the Periodic Table of the Elements (Mendeleev), C represents an element of the 2nd period of the Periodic Table of the Elements (Mendeleev), x is a number from 1 to 3, y is a number from 0 to 3 and z is a number from 1 to 12.

2. The process of claim 1, wherein the heterogeneous promoter is used in an amount of from 0.001 to 50% by weight, based on the amount of the aromatic hydroxy compound, if the promoter is used as a suspension, or a weight hourly space velocity of from 0.1 to 20 g of aromatic hydroxy compound per g of promoter and hour is set if the promoter is arranged in a fixed bed.

3. The process of claim 1, wherein, in the formula $A_xB_yC_z$ for the promoter, C is an element from the group of boron, carbon, nitrogen and oxygen.

4. The process of claim 3, wherein the promoter is a metal oxide, carbide, nitride or boride or a carbon-containing material.

5. The process of claim 1, wherein the reactor used for carrying out the process is a stirred vessel or a bubble column or a cascade of such reactors, with the cascade comprising from 2 to 15 individual reactors.

6. The process of claim 1, wherein the platinum metal is palladium.

7. The process of claim 6, wherein the palladium is present in the form of palladium compounds.

8. The process of claim 7, wherein the palladium is present in the form of palladium bromide or palladium acetylacetonate.

9. The process of claim 1, wherein the aromatic hydroxy compound is substituted or unsubstituted phenol.

10. The process of claim 9, wherein the organic hydroxy compound used is unsubstituted phenol.

11. The process of claim 1, wherein the base used is a tertiary amine, alkali metal phenoxide or alkali metal salt of a weak acid.

12. The process of claim 1, wherein the quaternary salt used is a tetraalkyl-ammonium or tetraalkylphosphonium salt.

13. The process of claim 11, wherein the base used is an alkali metal carboxylate or phenoxide.

14. The process of claim 12, wherein the quaternary salt used is a tetraalkyl-ammonium salt.

15. The process of claim 1, wherein diphenyl carbonate is prepared from phenol, CO and oxygen in the presence of sodium phenoxide, tetrabutyl-ammonium bromide and a catalyst.

16. The process of claim 2, wherein the heterogeneous promoter is used in an amount of from 0.01 to 10% by weight, based on the amount of the aromatic hydroxy compound, if the promoter is used as a suspension, or a weight hourly space velocity of from 0.2 to 10 g of aromatic hydroxy compound per g of promoter and hour is set if the promoter is arranged in a fixed bed.

17. The process of claim 16, wherein the heterogeneous promoter is used in an amount of from 0.1 to 5% by weight, based on the amount of the aromatic hydroxy compound, if the promoter is used as a suspension, or a weight hourly space velocity of from 0.2 to 5 g of aromatic hydroxy compound per g of promoter and hour is set if the promoter is arranged in a fixed bed.

18. The process of claim 1, which is carried out at from 30° to 150° C.

19. The process of claim 1, which is carried out at from 2 to 50 bar.

20. The process of claim 19, which is carried out at from 5 to 25 bar.

* * * * *